(12) United States Patent
Mathews et al.

(10) Patent No.: US 12,029,403 B2
(45) Date of Patent: Jul. 9, 2024

(54) SNARE DEVICE

(71) Applicant: Carnelian Medical LLC, Walpole, MA (US)

(72) Inventors: Eric D. Mathews, Walpole, MA (US); Mark W. I. Webster, Auckland (NZ)

(73) Assignee: CARNELIAN MEDICAL LLC, Walpole, MA (US)

( * ) Notice: Subject to any disclaimer, the term of this patent is extended or adjusted under 35 U.S.C. 154(b) by 55 days.

(21) Appl. No.: 17/687,069

(22) Filed: Mar. 4, 2022

(65) Prior Publication Data
US 2022/0280145 A1 Sep. 8, 2022

Related U.S. Application Data

(60) Provisional application No. 63/156,411, filed on Mar. 4, 2021.

(51) Int. Cl.
*A61B 17/00* (2006.01)
(52) U.S. Cl.
CPC ............... *A61B 17/00234* (2013.01); *A61B 2017/00358* (2013.01)
(58) Field of Classification Search
CPC .......... A61B 17/00234; A61B 17/50; A61B 2017/00358; A61B 2017/00526; A61B 17/221; A61B 2017/2212; A61M 23/24
See application file for complete search history.

(56) References Cited

U.S. PATENT DOCUMENTS

| 5,154,705 A | * | 10/1992 | Fleischhacker .... A61B 17/3207 600/585 |
| 5,171,233 A | | 12/1992 | Amplatz et al. |
| 5,387,219 A | * | 2/1995 | Rappe ................. A61B 17/221 606/1 |
| 5,522,819 A | * | 6/1996 | Graves ................ A61B 17/221 606/113 |
| 5,551,443 A | | 9/1996 | Sepetka et al. |
| 6,074,378 A | | 6/2000 | Mouri et al. |

(Continued)

OTHER PUBLICATIONS

International Search Report dated May 26, 2022, in PCT Application No. PCT/US22/18983, the corresponding PCT application to the present application.

(Continued)

*Primary Examiner* — Anh T Dang
(74) *Attorney, Agent, or Firm* — KRIEGSMAN & KRIEGSMAN

(57) ABSTRACT

A snare device for retrieving and/or manipulating an object within a space, such as a body lumen. In one embodiment, the snare device includes a support and a core wire. The support includes a proximal portion terminating in a proximal end, a distal portion terminating in a distal end, and a lumen, the lumen extending distally from the proximal end. The core wire is flexible and includes a proximal portion and a distal portion. The distal portion of the core wire and the distal portion of the support are complementarily shaped and are fixedly fitted together, wherein the core wire forms a loop extending away from the distal end of the support, and wherein the core wire passes through the lumen and emerges from the proximal end of the support. The distal portion of the support and the distal portion of the core wire may be complementarily dimensioned helical structures.

16 Claims, 14 Drawing Sheets

(56) References Cited

U.S. PATENT DOCUMENTS

| | | |
|---|---|---|
| 6,391,018 B1 | 5/2002 | Tanaka et al. |
| 6,500,185 B1 | 12/2002 | Mathews et al. |
| 6,554,842 B2 | 4/2003 | Heuser et al. |
| 6,620,172 B1 | 9/2003 | Dretler et al. |
| 6,652,536 B2 | 11/2003 | Mathews et al. |
| 7,058,456 B2 | 6/2006 | Pierce |
| 11,350,956 B2 | 6/2022 | Mathews |
| 2002/0161397 A1* | 10/2002 | Mathews ............ A61B 17/221 606/200 |
| 2006/0100544 A1* | 5/2006 | Ayala ................. A61M 25/09 600/585 |
| 2006/0229638 A1 | 10/2006 | Abrams et al. |
| 2008/0228209 A1 | 9/2008 | DeMello et al. |
| 2009/0209987 A1 | 8/2009 | Mathews et al. |
| 2012/0004647 A1* | 1/2012 | Cowley ............... A61B 17/221 606/1 |
| 2013/0184738 A1 | 7/2013 | Aroya et al. |
| 2014/0364866 A1* | 12/2014 | Dryden ............ A61B 17/32056 606/113 |
| 2015/0290432 A1 | 10/2015 | Mathews et al. |
| 2017/0224365 A1 | 8/2017 | Muyari et al. |
| 2020/0001053 A1 | 1/2020 | Rafiee |
| 2020/0008926 A1 | 1/2020 | Power |
| 2020/0330112 A1 | 10/2020 | Verma et al. |

OTHER PUBLICATIONS

Written Opinion dated May 26, 2022, in PCT Application No. PCT/US22/18983, the corresponding PCT application to the present application.

Reedlunn et al., "Superelastic shape memory alloy cables: Part I—Isothermal tension experiments," International Journal of Solids and Structures, 50:3009-3026 (2013).

U.S. Appl. No. 17/631,548, inventor Mathews, filed Jan. 31, 2022 (available in USPTO's IFW system).

* cited by examiner

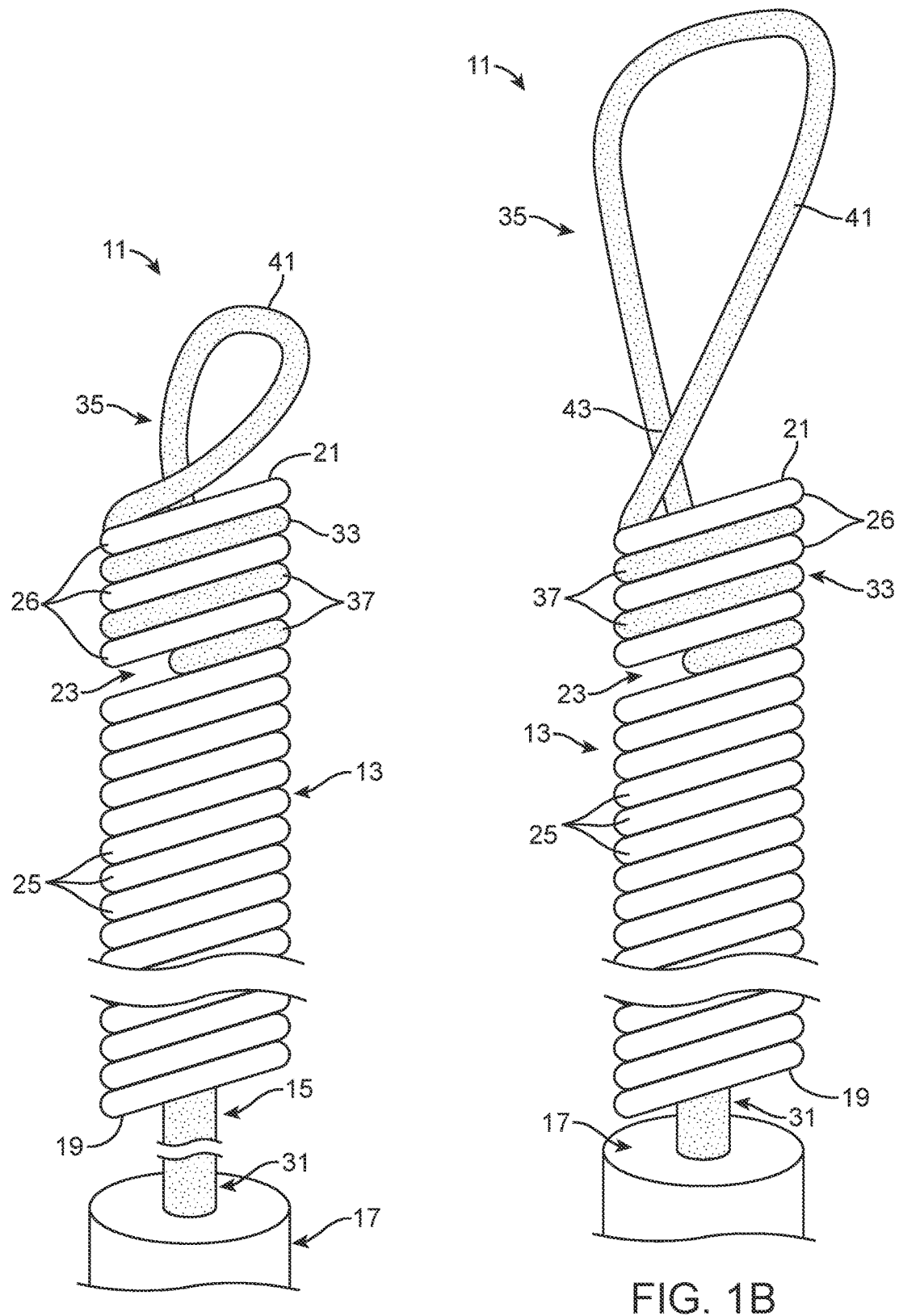

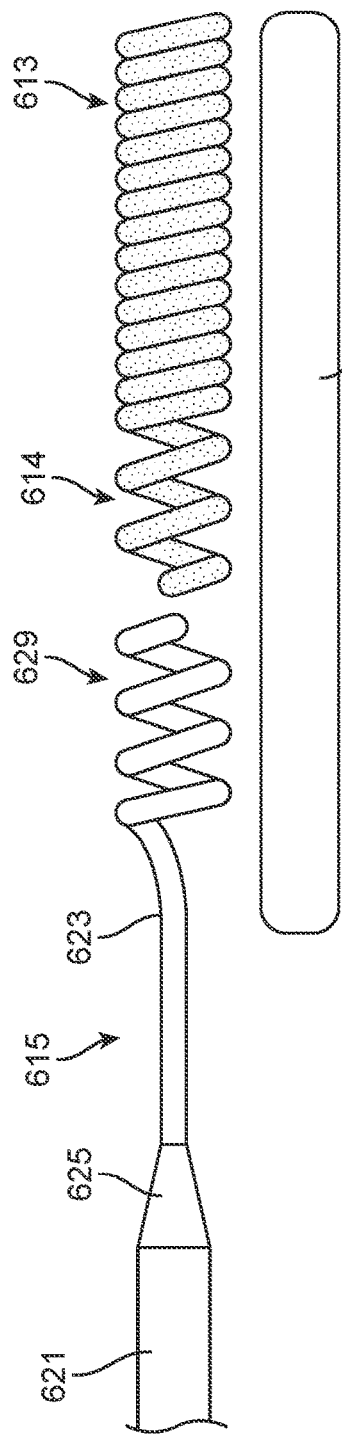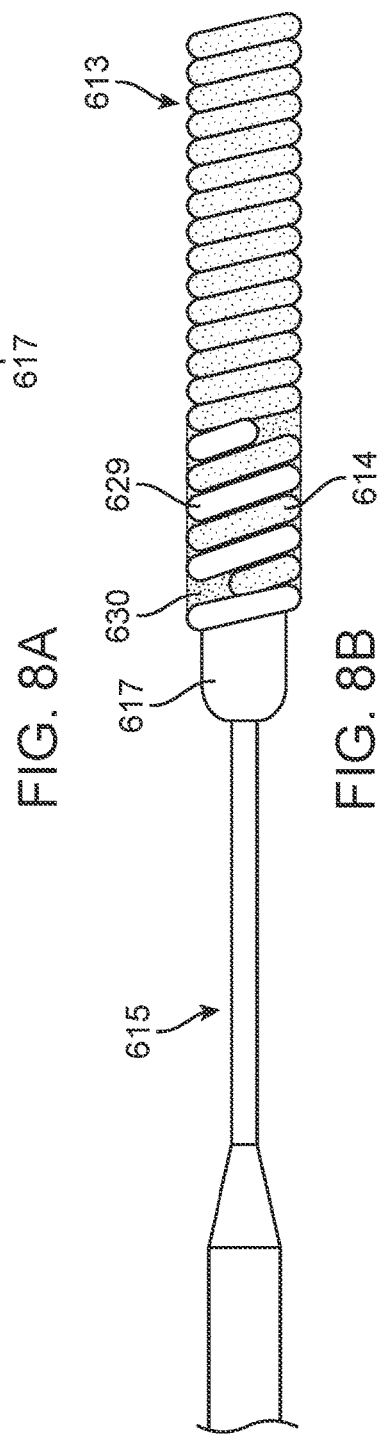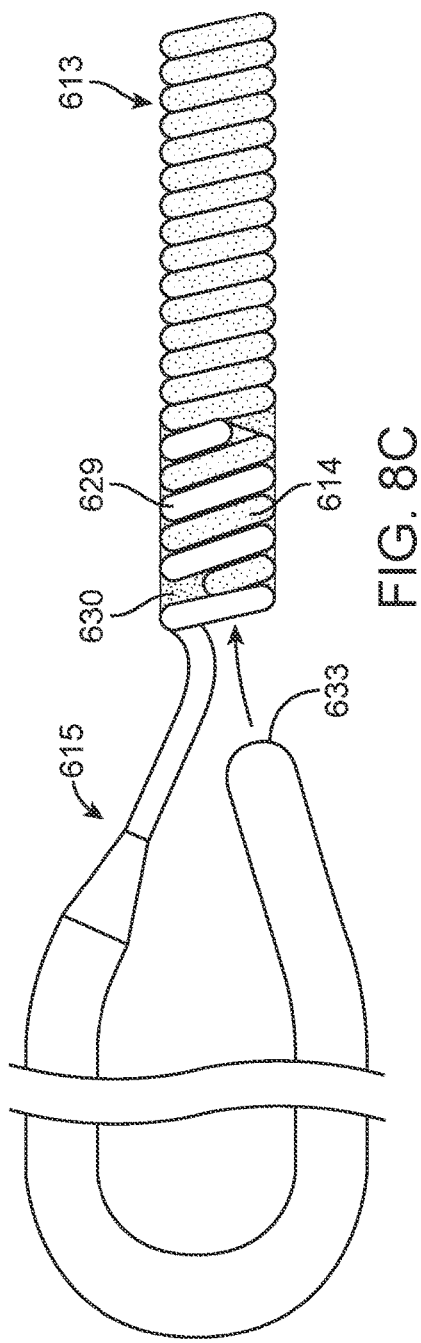

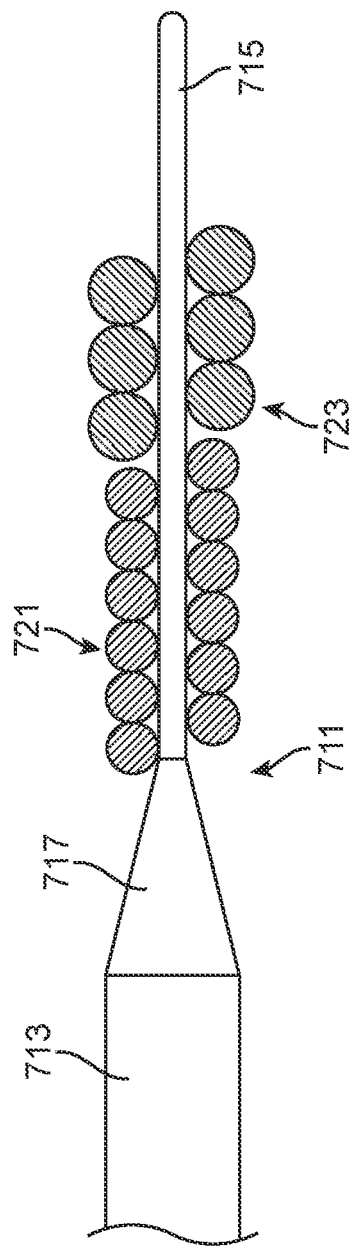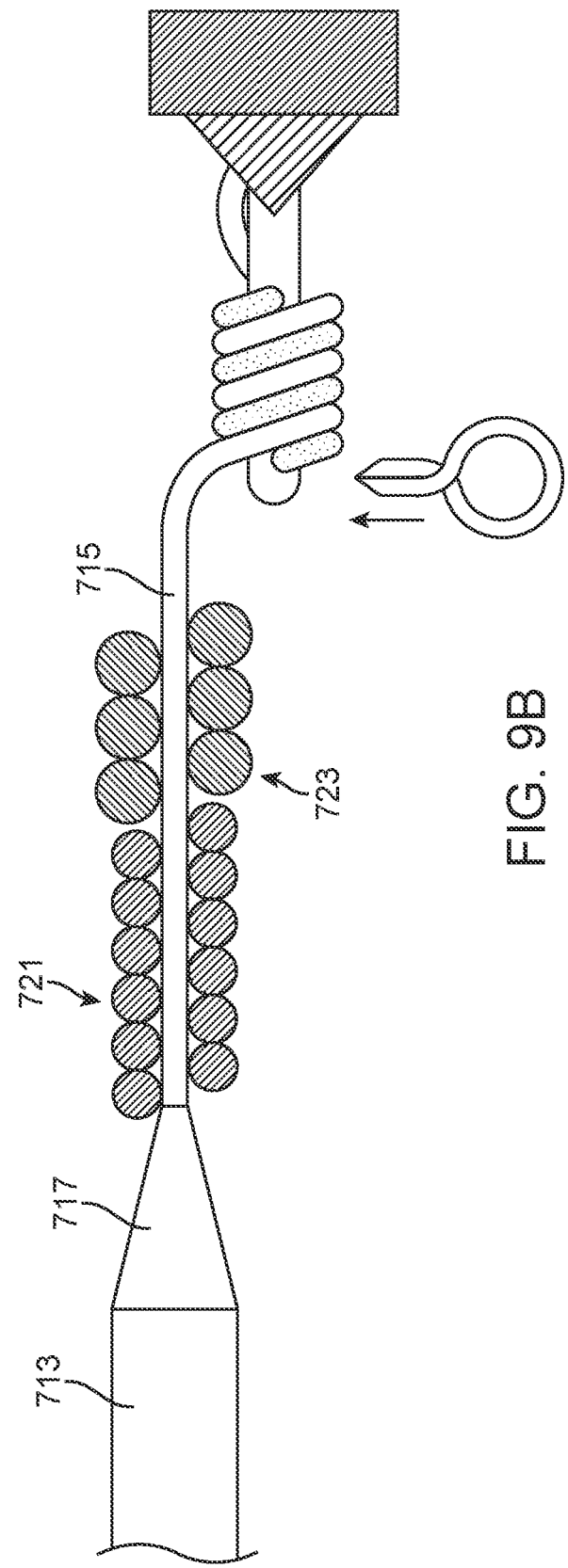
FIG. 9A
FIG. 9B

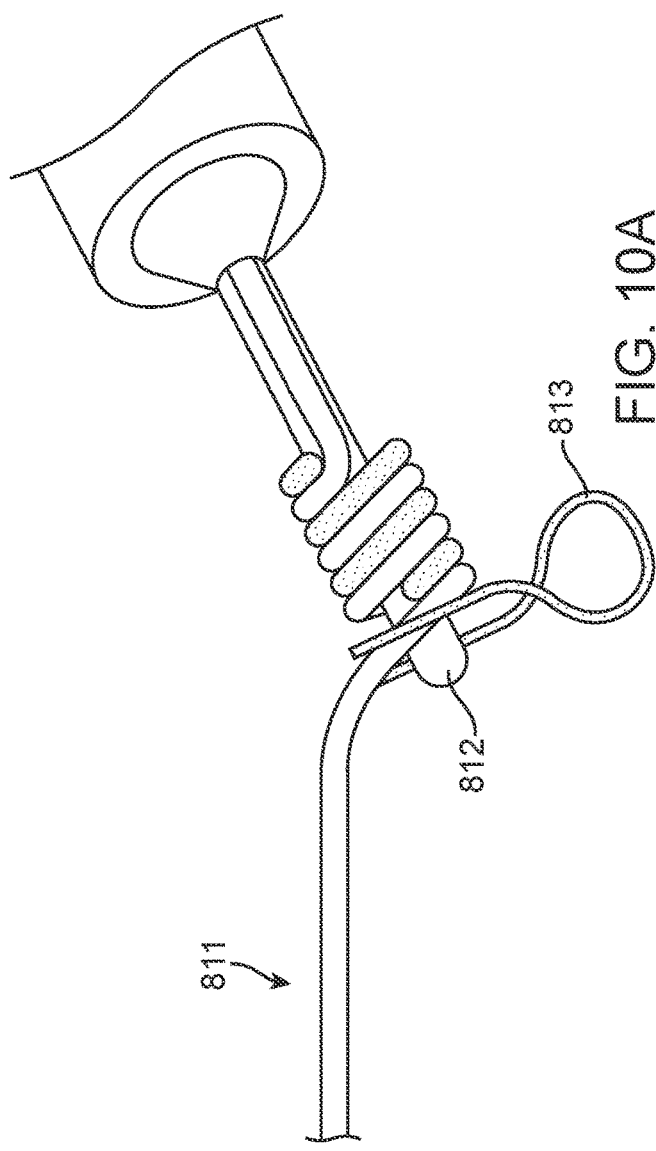
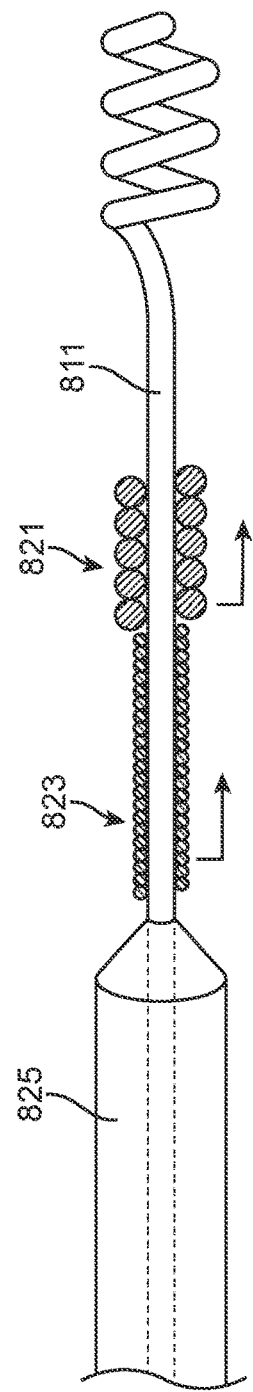
FIG. 10A
FIG. 10B

Loop Snare Designs and Dimensional Options

Support member - Sleeve over coil / Corewire w/ PTFE spray

| Fr | OD (.006" wall) | Coil OD | Coil Wire d/t | Coil ID | Gap for PTFE coat | NiTi Dia | Distal Dia for mating with coil |
|---|---|---|---|---|---|---|---|
| 2.7 | 0.0348 | 0.0336 | 0.006 | 0.0216 | 0.002 | 0.0196 | 0.006 |
| 2.1 | 0.0275 | 0.0263 | 0.005 | 0.0163 | 0.0015 | 0.0148 | 0.005 |
| 1.8 | 0.0239 | 0.0227 | 0.0045 | 0.0137 | 0.00155 | 0.01215 | 0.0045 |
| 1.5 | 0.0193 | 0.0181 | 0.0035 | 0.0111 | 0.0013 | 0.0098 | 0.0035 |
| 1.2 | 0.015 | 0.0138 | 0.0025 | 0.0088 | 0.0013 | 0.0075 | 0.0025 |
| 1.1 | 0.014 | 0.0128 | 0.0023 | 0.0082 | 0.0012 | 0.007 | 0.0023 |

Support member - PTFE Spray on OD / PI tube within Support / Corewire w/ PTFE spray

| Fr | OD w/ PTFE coat | Coil OD | Coil Wire d/t | Coil ID | PI OD | PI ID | Gap for PTFE coat | NiTi Dia | Distal Dia for mating with coil |
|---|---|---|---|---|---|---|---|---|---|
| 2.6 | 0.0343 | 0.0336 | 0.006 | 0.0216 | 0.021 | 0.019 | 0.003 | 0.016 | 0.006 |
| 2.1 | 0.027 | 0.0263 | 0.005 | 0.0163 | 0.015 | 0.013 | 0.0032 | 0.0098 | 0.005 |
| 1.8 | 0.0234 | 0.0227 | 0.0045 | 0.0137 | 0.013 | 0.011 | 0.0035 | 0.0075 | 0.0045 |
| 1.4 | 0.0188 | 0.0181 | 0.0035 | 0.0111 | 0.0105 | 0.009 | 0.002 | 0.007 | 0.0035 |
| 1.1 | 0.0145 | 0.0138 | 0.0025 | 0.0088 | 0.0085 | 0.007 | 0.001 | 0.006 | 0.0025 |

Support member - PTFE Spray on OD / Adhesive prevents stretching / Corewire w/ PTFE spray

| Fr | OD w/ PTFE coat | Coil OD | Coil Wire d/t | Coil ID | Gap for PTFE coat | NiTi Dia | Distal Dia for mating with coil |
|---|---|---|---|---|---|---|---|
| 2.6 | 0.0343 | 0.0336 | 0.006 | 0.0216 | 0.002 | 0.0196 | 0.006 |
| 2.1 | 0.027 | 0.0263 | 0.005 | 0.0163 | 0.0015 | 0.0148 | 0.005 |
| 1.8 | 0.0234 | 0.0227 | 0.0045 | 0.0137 | 0.00155 | 0.01215 | 0.0045 |
| 1.4 | 0.0188 | 0.0181 | 0.0035 | 0.0111 | 0.0013 | 0.0098 | 0.0035 |
| 1.1 | 0.0145 | 0.0138 | 0.0025 | 0.0088 | 0.0013 | 0.0075 | 0.0025 |
| 1.0 | 0.0135 | 0.0128 | 0.0023 | 0.0082 | 0.0012 | 0.007 | 0.0023 | d/t = diameter or thickness (flat wire)

FIG. 13

SNARE DEVICE

CROSS-REFERENCE TO RELATED APPLICATIONS

The present application claims the benefit under 35 U.S.C. 119(e) of U.S. Provisional Patent Application No. 63/156,411, inventors Eric D. Mathews et al., filed Mar. 4, 2021, the disclosure of which is incorporated herein by reference in its entirety.

BACKGROUND OF THE INVENTION

The present invention relates generally to snare devices and relates more particularly to a novel snare device.

There are many situations in which it may be desirable to grasp, to retrieve and/or to manipulate an object located within a confined space. For example, in the field of medicine, particularly in the field of minimally invasive surgery, it may be desirable, in some instances, to grasp, to retrieve and/or to manipulate an object or growth within a body lumen, such as a blood vessel. To this end, a number of different types of snare devices have been devised.

One common type of snare device comprises a wire, the wire typically being made of a shape memory material and being fixed to itself to form a distal loop that is reversibly transformable between an expanded state and a collapsed state. The foregoing wire is typically used in combination with a catheter, the catheter comprising a lumen through which the distal loop may be slidably inserted while in its collapsed state. As the wire is moved distally relative to the catheter, the portion of the distal loop that emerges distally beyond the catheter opens from its collapsed state to its expanded state. (In some snares, commonly referred to as "gooseneck snares," the loop is oriented perpendicular to the lumen of the catheter.) Conversely, as the wire is moved proximally relative to the catheter, the portion of the distal loop that is drawn into the catheter closes from its expanded state to its collapsed state. Consequently, the snare device may be used to capture an object by positioning the wire distally relative to the catheter so that the distal loop loosely surrounds the object and then by moving the wire proximally relative to the catheter until the distal loop tightens around the object.

An example of the foregoing type of snare device is disclosed in U.S. Pat. No. 5,171,233, inventors Amplatz et al., which issued Dec. 15, 1992, and which is incorporated herein by reference. More specifically, this patent discloses a snare having an elongate proximal member and a distal segment carried adjacent the distal end of the proximal member. The distal segment is in the shape of a loop oriented at an angle to the adjacent portion of the proximal member. The proximal member desirably comprises two segments of the wire which forms the distal segment, which may be bonded to one another. An exterior sheath may also be carried around this unified wire construction to reduce friction with the catheter. The wire is formed of a shape memory material, such as a superelastic nickel-titanium alloy. The superelastic shape memory property of the material allows the wire segments defining the distal segment to be straightened and collapsed upon one another into an elastically deformed configuration to pass through the lumen of a catheter and yet to automatically open into the original, unrestrained configuration upon emerging from the distal tip of the catheter.

A shortcoming with a snare device of the aforementioned type is that the distal loop, when positioned completely beyond the distal end of the catheter, has a fixed loop size. Consequently, if it is desired to have a variety of different loop sizes, one must have a plurality of differently sized snare devices. Additionally, another shortcoming is that, because a catheter must be inserted over the looped wire to tighten the loop around an object, the catheter adds radial size to the device, making the overall diameter of the device relatively large compared to the diameter of the wire. This is undesirable because it results in larger than necessary entry sites, thereby potentially leading to complications, such as excessive bleeding and/or hematomas. Furthermore, yet another shortcoming is that, when pulling the loop back into the catheter (or advancing the catheter over the loop), the loop tends to close or to collapse in an unpredictable manner, with the loop angle changing as it enters the catheter, often resulting in the object that is being grasped escaping the loop.

Another common type of snare device comprises a wire and a catheter, one end of the wire being secured to the outside of the distal end of the catheter, the other end of the wire being threaded proximally through the catheter and extending out of the proximal end of the catheter, with the portion of the wire extending distally out of the catheter forming a loop. The size of the loop may be adjusted, for example, by pushing the wire distally relative to the catheter to increase the size of the loop or by pulling the wire proximally relative to the catheter to decrease the size of the loop. Accordingly, the snare device may be used to capture an object by pushing the wire distally relative to the catheter so that the loop expands, positioning the expanded loop so that it loosely surrounds the object, and then by pulling the wire proximally relative to the catheter until the loop tightens around the object.

An example of the foregoing type of snare device is disclosed in U.S. Pat. No. 5,387,219, inventor Rappe, which issued Feb. 7, 1995, and which is incorporated herein by reference. More specifically, this patent discloses a device for retrieving foreign bodies, such as vasoocclusive coil or elements, from within vessels such as those of the cardiovascular system includes a tubular member and a flexible wire that extends axially through the tubular member with its distal end extending out the distal end of the tubular member and looped back and affixed to the distal end of the tubular member to form a loop whose size may be adjusted by axial movement of the wire relative to the tubular member and which may be used to ensnare the foreign bodies and remove them from the vessel.

A shortcoming with a snare device of the aforementioned type is that the manner of attaching the wire to the catheter, namely, by securing the distal end of the wire to the exterior (or interior) of the catheter, adds to the diameter of the overall device, specifically at the distal end. Having a large diameter at the distal end is not desirable for use in smaller vessels.

Therefore, to summarize, snares are often used to capture and retrieve intravascular objects. These objects have a wide range of shapes and sizes. The arteries, veins or heart chambers in which they are lodged also vary considerably in shape and size, as does the intravascular route which must be traversed to reach the object. Guide catheters or guiding sheaths are often used to deliver the snare close to the object to be snared and to aid directional manipulation of the snare loop once close to the object. With typical gooseneck snares, the distal loop is fully opened, the loop is manipulated over a graspable portion of the object, and the loop is closed. Not being able to adjust the size of the loop limits the combination of options (advancing, withdrawing and rotating the snare and/or the guide catheter or guiding sheath) which can be undertaken to grasp the object. In addition, clinicians may not know the ideal loop size to capture the object and, even if or once they do know, clinicians may have to use a snare that is not of a preferred diameter. To provide perspective, snares are not high volume items, and a gooseneck snare made by one company is sold in 10 different loop diameters. Interventional units stocking this product would be unlikely to hold more than two or perhaps three different loop diameters. Moreover, there is also a need for snares having a very small overall diameter, such as a snare having a diameter of no more than 0.014 inch. Such a snare may be useful, for example, in retrieving a stent in a coronary, cerebral or other small vessel.

Other documents that may be of interest may include the following, all of which are incorporated herein by reference: U.S. Pat. No. 7,058,456 B2, inventor Pierce, which issued Jun. 6, 2006; U.S. Pat. No. 6,652,536 B2, inventors Mathews et al., which issued Nov. 25, 2003; U.S. Pat. No. 6,620,172 B1, inventors Dretler et al., which issued Sep. 16, 2003; U.S. Pat. No. 6,554,842 B2, inventors Heuser et al., which issued Apr. 29, 2003; U.S. Pat. No. 6,500,185 B1, inventors Mathews et al., which issued Dec. 31, 2002; U.S. Pat. No. 6,391,018 B1, inventors Tanaka et al., which issued May 21, 2002; U.S. Pat. No. 6,074,378, inventors Mouri et al., which issued Jun. 13, 2000; U.S. Pat. No. 5,551,443, inventors Sepetka et al., which issued Sep. 3, 1996; U.S. Pat. No. 5,522,819, inventors Graves et al., which issued Jun. 4, 1996; U.S. Patent Application Publication No. US 2020/0008926 A1, inventor Power, which was published Jan. 9, 2020; U.S. Patent Application Publication No. US 2009/0209987 A1, inventors Mathews et al., which was published Aug. 20, 2009; U.S. Patent Application Publication No. US 2008/0228209 A1, inventors DeMello et al., which was published Sep. 18, 2008; and U.S. Patent Application Publication No. US 2006/0229638 A1, inventors Abrams et al., which was published Oct. 12, 2006.

SUMMARY OF THE INVENTION

It is an object of the present invention to provide a novel snare device.

It is another object of the present invention to provide a snare device as described above that overcomes at least some of the shortcomings associated with existing snare devices.

It is still another object of the present invention to provide a snare device as described above that is easy to manufacture, that is easy to use, and that has a minimal number of parts.

Therefore, according to one aspect of the invention, there is provided a snare device, the snare device comprising (a) a support, the support comprising a proximal portion terminating in a proximal end, a distal portion terminating in a distal end, and a lumen, the lumen extending distally from the proximal end; and (b) a core wire, the core wire being flexible and comprising a proximal portion and a distal portion, wherein the distal portion of the core wire and the distal portion of the support are complementarily shaped and are fixedly fitted together, wherein the core wire forms a loop extending away from the distal end of the support, and wherein the core wire passes through the lumen and emerges from the proximal end of the support.

In a more detailed feature of the invention, the distal portion of the support and the distal portion of the core wire may be complementarily dimensioned helical structures.

In a more detailed feature of the invention, the lumen of the support may have a longitudinal axis, and the loop may extend generally along the longitudinal axis.

In a more detailed feature of the invention, the lumen of the support may have a longitudinal axis, and the loop may extend generally perpendicular relative to the longitudinal axis.

In a more detailed feature of the invention, the lumen of the support may extend from the proximal end of the support to the distal end of the support, and the core wire may pass through the distal end of the support.

In a more detailed feature of the invention, the support may have a side opening, and the core wire may pass through the side opening.

In a more detailed feature of the invention, the support may comprise a coil, and the coil may comprise a proximal portion having closely spaced turns and a distal portion having spaced apart turns.

In a more detailed feature of the invention, the support may comprise a coil and a hypotube, and the coil may be mounted on a distal portion of the hypotube.

In a more detailed feature of the invention, the snare device may further comprise a handle, and the proximal portion of the core wire may be coupled to the handle.

In a more detailed feature of the invention, the snare device may further comprise a sleeve, and the sleeve may be positioned coaxially around the support.

In a more detailed feature of the invention, the snare device may further comprise a tube, and the tube may be positioned coaxially within the support.

In a more detailed feature of the invention, the snare device may further comprise a radiopaque coil, and the radiopaque coil may be mounted coaxially around the core wire.

In a more detailed feature of the invention, the core wire may consist of a single filament.

In a more detailed feature of the invention, the core wire may comprise a drawn filled tube coaxially surrounding a radiopaque wire.

In a more detailed feature of the invention, the core wire may further comprise a tube coaxially surrounding a proximal portion of the drawn filled tube.

In a more detailed feature of the invention, the core wire may comprise a wire cable and a tube, and the tube may coaxially surround a proximal portion of the wire cable.

In a more detailed feature of the invention, the snare device may further comprise two radiopaque coils coaxially mounted over the core wire, a first of the two radiopaque coils may be positioned more proximally on the core wire and may have an outer diameter smaller than the diameter of the lumen, and a second of the two radiopaque coils may be positioned more distally on the core wire and may have an outer diameter greater than the diameter of the lumen.

In a more detailed feature of the invention, the loop may be adjusted in size by moving the proximal end of the core wire relative to the proximal end of the support.

In a more detailed feature of the invention, the distal portion of the core wire and the distal portion of the support may be flush with one another.

The present invention is also directed at methods of making and using the snare device of the present invention.

For purposes of the present specification and claims, various relational terms like "top," "bottom," "proximal," "distal," "upper," "lower," "front," and "rear" may be used to describe the present invention when said invention is positioned in or viewed from a given orientation. It is to be understood that, by altering the orientation of the invention, certain relational terms may need to be adjusted accordingly.

Additional objects, as well as features and advantages, of the present invention will be set forth in part in the description which follows, and in part will be obvious from the description or may be learned by practice of the invention. In the description, reference is made to the accompanying drawings which form a part thereof and in which is shown by way of illustration various embodiments for practicing the invention. The embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. These drawings are not necessarily drawn to scale, and certain components may have undersized and/or oversized dimensions for purposes of explication. In the drawings wherein like reference numerals represent like parts:

FIGS. 1A and 1B are fragmentary perspective views of a first embodiment of a snare device constructed according to the teachings of the present invention, the snare device being shown with its loop in a comparatively more contracted state and in a comparatively more expanded state, respectively;

FIGS. 8A through 8C represent a sequence of views illustrating one embodiment of a method of assembling a snare device according to the teachings of the present invention;

FIGS. 9A and 9B represent a sequence of views illustrating one embodiment of a method for mounting one or more radiopaque coils over a core wire according to the teachings of the present invention;

FIGS. 10A and 10B represent a sequence of views illustrating another embodiment of a method for mounting one or more radiopaque coils over a core wire according to the teachings of the present invention;

FIG. 13 shows various exemplary design options and dimensions for the snare device of the present invention.

DETAILED DESCRIPTION OF THE INVENTION

Figure 1C:
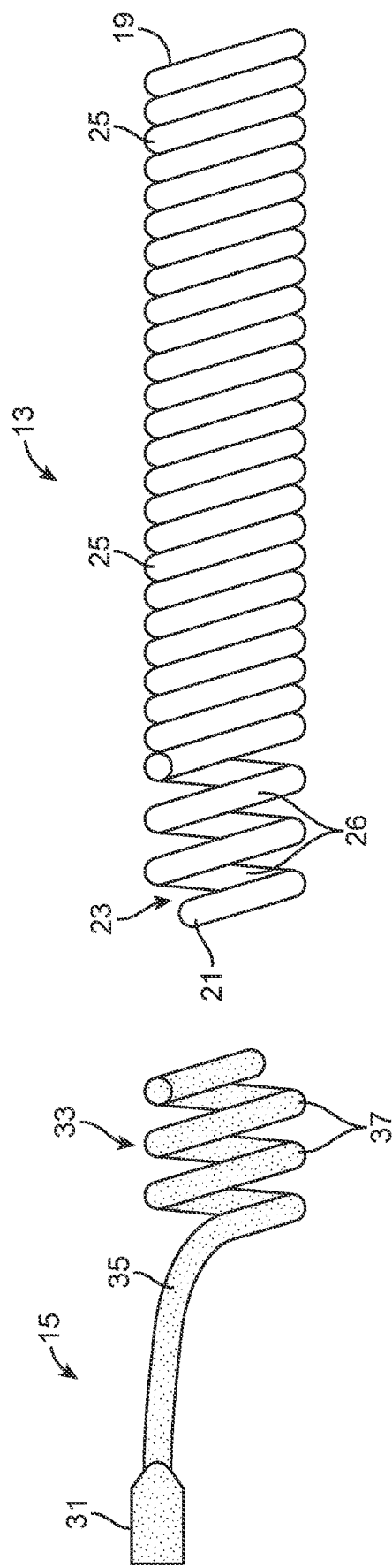
FIG. 1C is a fragmentary side view showing the support and the core wire of the snare device of FIG. 1A, with the support and the core wire being shown disassembled and with the core wire being shown without being looped.

The present invention relates to a snare device for retrieving and/or manipulating an object within a space, the space being, for example, a body lumen ranging in size from a small, tortuous, vascular structure to a larger vessel, organ, cavity, etc. In at least some embodiments, the snare device may comprise a support and a core wire. More specifically, in at least some embodiments, at least a portion of the support may be hollow, and a first portion of the core wire may be joined, for example, using one or more complementary or mating features or structures, to a distal end of the support, a second portion of the core wire may extend from the support, and a third portion of the core wire may extend into the support and may be adapted to slide relative to the support, whereby the core wire may form a looped structure, extending from the support, the size of the looped structure being adjusted by sliding the core wire relative to the support.

In at least some embodiments, the distal end of the support may comprise a tubular member and may additionally comprise an angular slot in a wall of the tubular member that can appear helical if the angular slot traverses a significant angular rotation. A distal end of the core wire may be formed into a shape that mates with the angular slot in the support. For example, in at least some embodiments, the distal end of the support and the distal end of the core wire may be shaped as complementary or mating helices. The support and the core wire may be joined together in a process that comprises inserting a mandrel between the support and the core wire and rotating the helical end of the core wire into the support. Preferably, the distal end of the core wire may be sized to fit roughly within the distal end of the support. The core wire may be assembled and joined to the support, leaving an open lumen at the distal end. The proximal end of the core wire may be introduced into the distal end of the support or a side opening in the support and then passed through the lumen of the support until it exits the proximal end of the support. In this manner, by pulling the core wire proximally, the loop may be made smaller; conversely, by pushing the core wire distally, the loop may be made larger. The size ratios of the core wire and the support may enable the overall device diameter to be as small as the smallest snare retrievers currently available and, in some cases, potentially smaller. For larger sized devices, the core wire can be made more robust if desired.

In at least some embodiments, the support may comprise a coil, which may be, for example, a metal coil, and the support coil may have a short stretch at its distal end. The support coil may be made of typical coiling wire materials including, for example, 304 stainless steel, MP35N (nickel-cobalt alloy), and Co/Cr alloys that are MRI safe. The support coil may comprise a round wire or a rectangular flat wire.

In at least some embodiments, a sleeve may be placed around the outside of the support coil, the sleeve serving to support the support coil and to prevent the support coil from elongating or skewing while retaining some flexibility therein. The sleeve placed around the coil may be made of materials like, for example, NYLON (polyamide), PEBAX (polyether block amide), PET (polyethylene terephthalate), PTFE (polytetrafluoroethylene), and the like. Instead of being placed around the outside of the support coil, a sleeve may be placed within the support coil. (Alternatively, a first sleeve may be placed around the outside of the support coil, and a second sleeve may be placed along the inside of the support coil.) Such a sleeve may include, for example, a PI (polyimide) or NYLON (polyamide) tube, which tube may also be coated with PTFE or another lubricious material on its inner surface. In another embodiment, a sleeve can be formed by a poured adhesive that bridges the coils of the support coil so as to minimize elongation yet remain flexible enough to allow bending.

In at least some embodiments, the support may comprise a tube or similar structure that may not be formed from one or more coiled members. For example, a metallic tube comprising a material such as, but not limited to, 304 stainless steel, Co/Cr alloy, and Nitinol (nickel-titanium alloy) may be modified to include a helical slot at its distal end. To add flexibility, the tube may be variably slotted as required. A plastic composite tube may also be used for the support, where materials like PI, PEBAX, PET, and PTFE can be used and/or combined with a metallic braid or coil. The distal end of the support tube may be modified to receive the helixed core wire, but such modification can readily be accomplished by methods and materials that are currently available and well-known.

In at least some embodiments, the core wire may comprise a single wire or may comprise a combination of wires and/or tubes. As an example of a single wire embodiment, the super-elastic material Nitinol may be used. The distal end of the core wire may be reduced in diameter by grinding and then set into a desired helix or other mating shape using a form tool and heat. For a helix with tight bend radiuses, a Nitinol wire may be heat treated or annealed to reduce stiffness according to standard methods. Adjacent to the distal helix, the Nitinol wire may be formed into a desired loop shape. For example, in a manner similar to a gooseneck snare, the core wire may be formed into a loop that resides somewhat perpendicular to the axis of the support. More proximally, the core wire may have a larger diameter, which may be useful for advancing and retracting the core wire to alter the size of the loop for capturing and grasping.

In at least some embodiments, the core wire may comprise several materials and/or structures. For example, the core wire may comprise a smaller diameter wire, which wire may be made of or may comprise Nitinol or the like and which may be sized and shaped to mate with the helical portion of the support. In addition, the core wire may also comprise a larger diameter tube, which tube may surround and be attached to the smaller diameter wire to facilitate the pushing and pulling of the core wire. The smaller diameter wire may, itself, be a composite of materials and/or structures. For example, the smaller diameter wire may comprise a Nitinol tube filled with a radiopaque core (e.g., Fort Wayne Metals DFT® wire), which may allow the grasping loop to be viewed under fluoroscopy. The larger diameter tube surrounding the smaller diameter wire may comprise one or more of Nitinol, stainless steel, and a polymer/metal composite, wherein the polymer/metal composite may comprise a combination of PI, PEBAX, NYLON, PTFE, metallic braid, or metallic coil.

Optionally, the snare device may further comprise a comparatively small coil placed around the grasping loop formed by the core wire. The aforementioned small coil may comprise a radiopaque material, such as, for example, various platinum, palladium or tungsten alloys, which may serve to facilitate viewing the loop under fluoroscopy. The outer diameter of this small coil preferably is sized to permit it to fit within the lumen of the support.

Optionally, the snare device may additionally or alternatively comprise an additional coil or a tubular member that may surround the core wire and that may be positioned just proximal to the helixed portion of the core wire, with the diameter of this additional coil or tubular member being sized to be larger than the lumen of the support. In this manner, the aforementioned additional coil or tubular member may limit how much of the core wire may be introduced into the lumen of the support and, in so doing, may limit the tightness of the angular bending in the loop. Very tight angular bending of a Nitinol loop can result in wire fracture, particularly when several cycles of tight bending are applied to the loop. The above-described additional coil or tubular member may be formed of the same or similar materials described above.

As alluded to above, in at least some embodiments, the core wire used to form the loop may be fed proximally through an opening at the distal end of the support. In an alternative embodiment, the core wire used to form the loop may be fed proximally through a side opening in the support. While this arrangement may be sub-optimal as it increases the distal outer diameter of the device, such an arrangement may have a safety advantage of reducing the degree of angular bend required for the core wire and would reduce the risk of core wire fracture. Additionally, such an arrangement may result in the grasping shape being altered, which could be preferred for some anatomical configurations.

The proximal end of the core wire may serve as a handle to selectively advance or retract the portion of the core wire that forms the loop. The diameter of the core wire at its proximal end may be increased to the same diameter as the support, thereby serving to limit how far the core wire may be inserted and, thus, how much the loop may be extended or shaped. If the proximal end of the core wire is kept no larger than the diameter of the support, the device may additionally or alternatively be used as a guiding device or guidewire.

Another potential application of the snare device of the present invention may be as an anchoring device. For example, the snare device may be advanced through a guiding catheter and positioned within a vessel and then the loop may be enlarged within the vessel to a size larger than the vessel inner diameter. Preferably, the loop is positioned at a proximally acute angle so that, when tension is applied to the proximal end of the support, the loop provides resistance. When deployed in this manner, the snare device may provide purchase support to the guiding catheter, thereby allowing it to stay in place as other devices are advanced, instead of popping out of the ostium. Alternatively, the snare device, when deployed as an anchor, may provide a securely positioned rail over which a treatment catheter may be advanced.

Referring now to FIGS. 1A through 1C, there are shown fragmentary perspective views of a first embodiment of a snare device in a comparatively more contracted state and in a comparatively more expanded state, respectively, the snare device being constructed according to the teachings of the present invention and being represented generally by reference numeral 11. Details of snare device 11 that are discussed elsewhere in this application or that are not critical to an understanding of the invention may be omitted from one or more of FIGS. 1A through 1C and/or from the accompanying description herein or may be shown in one or more of FIGS. 1A through 1C and/or described herein in a simplified manner.

Snare device 11 may comprise a support 13, a core wire 15, and a handle 17.

Support 13 may be a unitary (i.e., one-piece) hollow member of generally cylindrical shape and may include a proximal end 19, a distal end 21, and a lumen 23, wherein lumen 23 may extend generally longitudinally between proximal end 19 and distal end 21. In the present embodiment, support 13 may comprise a coiled filament having a plurality of turns. The turns 25 at proximal end 19 of support 13 and along most of the length of support 13 may be in contact with or may be relatively closely spaced to the turns 25 directly proximal and distal thereto; however, for reasons to be discussed below, the turns 26 near distal end 21 of support 13 may have a short stretch, i.e., may be spaced apart from one another by a relatively greater distance.

In the present embodiment, support 13 may be, for example, a metal coil and may be made of typical coiling wire materials including, for example, 304 stainless steel, MP35N (nickel-cobalt alloy), and Co/Cr alloys that are MRI safe. The coiled wire used to form support 13 may be selected from any of a variety of differently shaped wires including, for example, a round wire or a rectangular flat wire.

Core wire 15 may be a unitary (i.e., one-piece), solid member and may comprise a proximal portion 31, a distal portion 33, and an intermediate portion 35. In the present embodiment, core wire 15 may be made of a shape memory material, such as Nitinol. Proximal portion 31 may be fixedly coupled to handle 17. Distal portion 33 may be fixedly coupled to support 13. More specifically, in the present embodiment, distal portion 33 may be in the shape of a coil having a plurality of turns 37. Preferably, the coil structure of distal portion 33 has an inner diameter that substantially matches that of support 13 and has an outer diameter that substantially matches that of support 13. In addition, the filamentary diameter of the wire used to form support 13 and the filamentary diameter of core wire 15 are substantially equal, and turns 37 of distal portion 33 are preferably spaced apart from one another by substantially the same pitch as turns 26 of support 13 so that turns 37 of distal portion 33 may be mated with and bonded to the turns 26 proximate to distal end 21 of support 13. The mating of core wire 15 with support 13 may be accomplished by screwing together turns 37 and turns 26.

Intermediate portion 35 of core wire 15, by virtue of being drawn through support 13, may form a distal looped portion 41 that may extend distally beyond support 13 and a relatively straight proximal portion 43 that may extend generally coaxially within support 13. In the present embodiment, looped portion 41 may be oriented so that enlargement of looped portion 41 may be generally parallel to the longitudinal axis of support 13.

As seen best in FIG. 1C, distal portion 33 of core wire 15 and intermediate portion 35 of core wire 15 may have a relatively smaller filamentary diameter, which may provide greater flexibility, whereas proximal portion 31 of core wire 15 may have a relatively larger filamentary diameter, which may help to resist flexure during pushing.

Handle 17 may be used to selectively move core wire 15 proximally and distally relative to support 13. As seen in FIG. 1A, when core wire 15 is in a more proximal position relative to support 13, looped portion 41 may be in a more contracted state (i.e., looped portion 41 may have a comparatively smaller size). By contrast, as seen in FIG. 1B, when core wire 15 is in a more distal position relative to support 13, looped portion 41 may be in a more expanded state (i.e., looped portion 41 may have a comparatively larger size). Accordingly, one may use snare device 11 to capture an object by positioning snare device 11 within a space near an object, moving core wire 15 distally relative to support 13 to surround the object with looped portion 41, and then retracting core wire 15 proximally relative to support 13 to tighten looped portion 41 around the object.

One advantage of snare device 11 relative to many conventional snare devices is that the overall diameter of the distal end of snare device 11 may be kept relatively small. This is, in part, because the distal end of core wire 15 may be secured to support 13 by being interlaced with support 13. Such an arrangement obviates the need to secure the distal end of the core wire to the interior or exterior of the support or to fold over at least a portion of the core wire within the support, all of which add radial size to the device. Another advantage of snare device 11 is that the mating of the helical structures of support 13 and core wire 15 promotes a very strong attachment between these two components, thereby minimizing the risk of detachment therebetween.

Figures 2A, 2B:
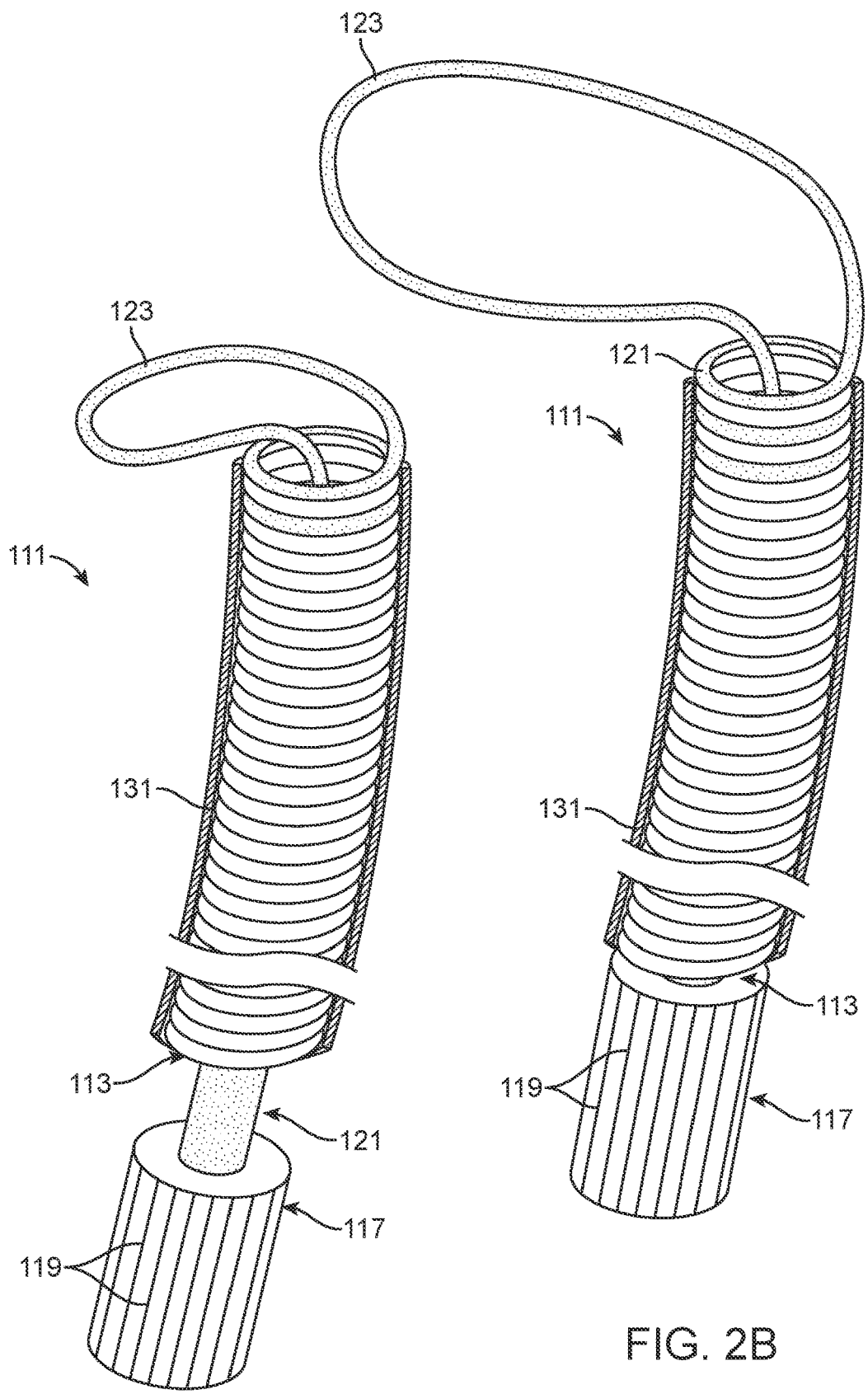
FIGS. 2A and 2B are fragmentary perspective views, partly in section, of a second embodiment of a snare device constructed according to the teachings of the present invention, the snare device being shown with its loop in a comparatively more contracted state and in a comparatively more expanded state, respectively.

Referring now to FIGS. 2A and 2B, there are shown fragmentary perspective views, partly in section, of a second embodiment of a snare device in a comparatively more contracted state and in a comparatively more expanded state, respectively, the snare device being constructed according to the teachings of the present invention and being represented generally by reference numeral 111. Details of snare device 111 that are discussed elsewhere in this application or that are not critical to an understanding of the invention may be omitted from one or more of FIGS. 2A and 2B and/or from the accompanying description herein or may be shown in one or more of FIGS. 2A and 2B and/or described herein in a simplified manner.

Snare device 111 may be similar in certain respects to snare device 11. For example, snare device 111 may comprise a support 113, which may be similar or identical to support 13, and may also comprise a handle 117, which may be similar or identical to handle 17. (In the present embodiment, handle 117 is shown having a plurality of longitudinal exterior ribs 119.)

Snare device 111 may also comprise a core wire 121. Core wire 121 may be similar in many respects to core wire 15, with one difference between the two core wires being that core wire 121 may be shaped to include a looped portion 123 that may extend generally perpendicularly relative to the longitudinal axis of support 113 whereas core wire 15 may be shaped to include a looped portion 41 that may extend generally along the longitudinal axis of support 13.

Snare device 111 may further comprise a sleeve 131. Sleeve 131, which may be a unitary (i.e., one-piece) tubular member made of a polymer, such as NYLON, PREBAX, PET, PTFE, or the like, may be snugly positioned coaxially around support 113. Sleeve 131, which may be heat-shrunk or otherwise compressed around support 113, may be used to prevent support 113 from elongating or skewing while still providing support 113 with some degree of flexibility.

Sleeve 131 may be transparent but need not be. Also, it is to be understood that sleeve 131 may be used in snare device 11.

Snare device 111 may be used in a generally analogous fashion to snare device 11. Because of the shape of looped portion 123, snare device 111 may be used in many of the types of applications where Gooseneck snares are desired.

Figures 3A, 3B:
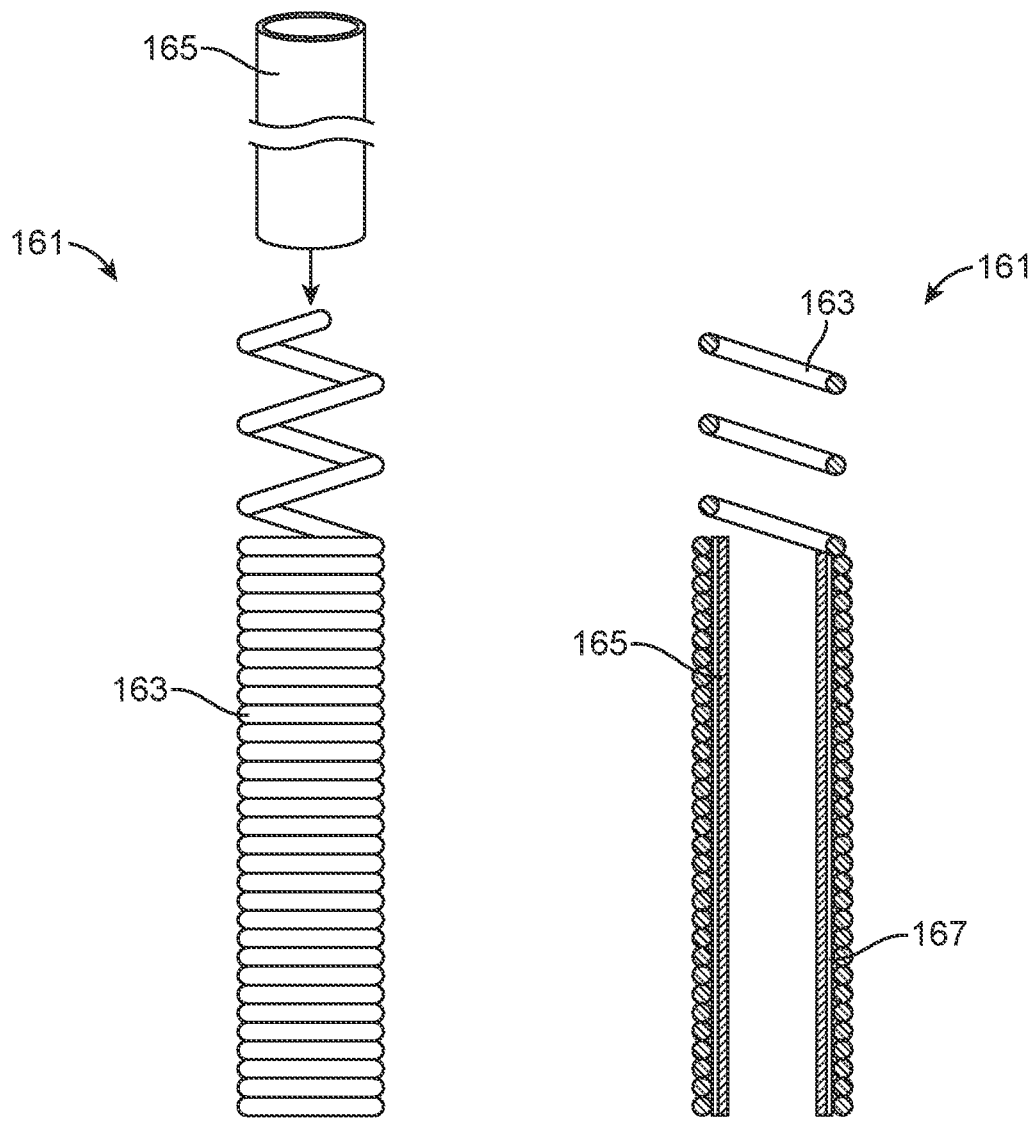
FIGS. 3A and 3B are fragmentary, partly exploded, side and simplified section views, respectively, of an alternative support and sleeve combination to that shown in FIGS. 2A and 2B.

Although, in snare device 111, sleeve 131 is positioned around the outside of support 113, it is to be understood that other types of sleeves may additionally or alternatively be used that may be positioned within support 113. For example, referring to FIGS. 3A and 3B, there are shown various views of an alternative combination of a support and sleeve to that shown in snare device 111, the combination being represented generally by reference numeral 161.

Combination 161 may comprise a support 163 and a sleeve 165. Support 163 may be identical to support 113. Sleeve 165 may be a unitary (i.e., one-piece) tubular member dimensioned to snugly fit within support 163. Sleeve 165 may be made of a polymeric material, such as a polyimide, and may have a lubricious coating, such as PTFE, on its interior surface. An adhesive 167 may be used to fix sleeve 165 within support 163.

It is to be understood that combination 161 may be used in snare device 11 in place of support 13.

As an alternative to using sleeves 131 and/or 165, one may use an adhesive to bond adjacent turns of supports 113 and 163, thereby minimizing the occurrence of elongation or skewing.

Figure 4:
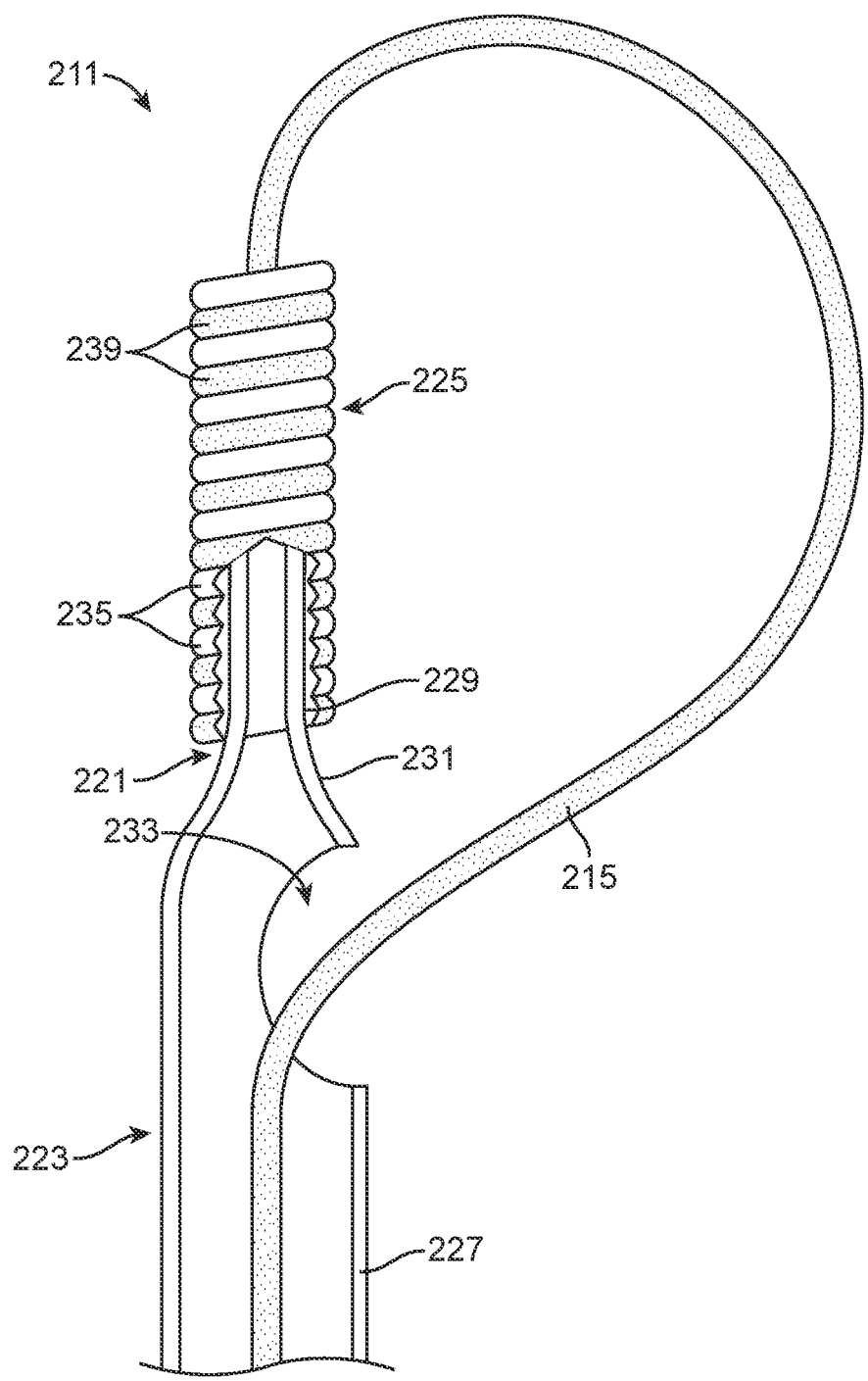
FIG. 4 is a fragmentary side view, partly in section and broken away in part, of a third embodiment of a snare device constructed according to the teachings of the present invention.

Referring now to FIG. 4, there is shown a fragmentary side view, partly in section and broken away in part, of a third embodiment of a snare device, the snare device being constructed according to the teachings of the present invention and being represented generally by reference numeral 211. Details of snare device 211 that are discussed elsewhere in this application or that are not critical to an understanding of the invention may be omitted from FIG. 4 and/or from the accompanying description herein or may be shown in FIG. 4 and/or described herein in a simplified manner.

Snare device 211 may be similar in certain respects to snare device 11. For example, snare device 211 may comprise a core wire 215, which may be similar or identical to core wire 15, and may also comprise a handle (not shown) coupled to the proximal end of core wire 215, which handle may be similar or identical to handle 17.

Snare device 211 may also comprise a support 221. Support 221, in turn, may comprise a proximal member 223 and a distal member 225. Proximal member 223 of support 221 may comprise a unitary (i.e., one-piece) tubular structure and, in the present embodiment, may be, for example, a stainless steel hypotube. Proximal member 223 may be shaped to include a proximal portion 227, a distal portion 229, and an intermediate portion 231. Proximal portion 227 may be a hollow cylindrical structure of comparatively greater diameter, distal portion 229 may be a hollow cylindrical structure of comparatively lesser diameter, and intermediate portion 231 may be a hollow structure whose diameter tapers from proximal portion 227 to distal portion 229. An opening 233 may be provided in the side of proximal portion 227, opening 233 being dimensioned to permit core wire 215 to freely pass therethrough.

Distal member 225 of support 221 may comprise a unitary (i.e., one-piece) hollow structure of generally cylindrical shape. More specifically, distal member 225 may comprise a coiled filament having a plurality of turns 235. In the present embodiment, distal member 225 may be made of, for example, stainless steel wire. At least some of turns 235 of distal member 225 may be spaced apart appropriately to mate with and to be bonded to the turns 239 located at a distal end of core wire 215 in a manner analogous to that discussed above in connection with snare device 11. Distal member 225 of support 221 may be coaxially inserted over proximal member 223 of support 221 and fixedly secured thereto. Preferably, the outer diameters of proximal member 223 and distal member 225 are similar.

Snare device 211 may be used in a generally analogous fashion to snare device 11.

One advantage of snare device 211, as compared to snare device 11, is that, due to the fact that core wire 215 is fed into support 221 through opening 233, as compared to being fed through the distal end of support 221, the degree of angular bend that may be required for core wire 215 may be reduced, thereby reducing the risk of core wire fracture (which fracture may present a safety hazard). Additionally, because of the manner in which core wire 215 is fed into support 221, snare device 211 may have a different loop shape than snare device 11, which difference may be preferred for some anatomical configurations. On the other hand, because of its construction, snare device 211 may have a larger outer diameter than snare device 11, which may be undesirable in some situations.

Figure 5:
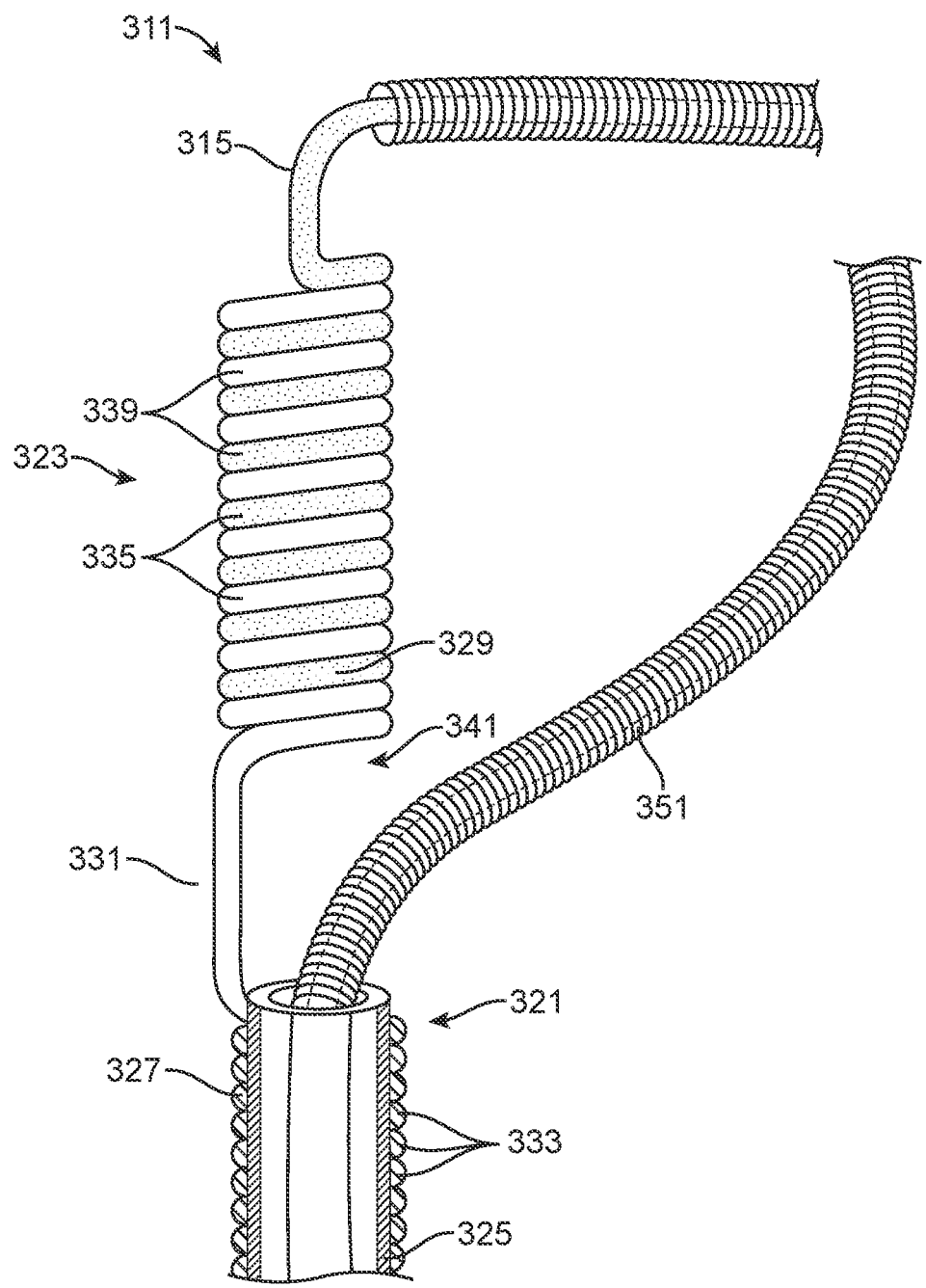
FIG. 5 is a fragmentary side view, partly in section, of a fourth embodiment of a snare device constructed according to the teachings of the present invention.

Referring now to FIG. 5, there is shown a fragmentary side view, partly in section, of a fourth embodiment of a snare device, the snare device being constructed according to the teachings of the present invention and being represented generally by reference numeral 311. Details of snare device 311 that are discussed elsewhere in this application or that are not critical to an understanding of the invention may be omitted from FIG. 5 and/or from the accompanying description herein or may be shown in FIG. 5 and/or described herein in a simplified manner.

Snare device 311 may be similar in certain respects to snare device 11. For example, snare device 311 may comprise a core wire 315, which may be similar or identical to core wire 15, and may also comprise a handle (not shown) coupled to the proximal end of core wire 315, which handle may be similar or identical to handle 17.

Snare device 311 may also comprise a support 321. Support 321, in turn, may comprise a coil 323 and a tube 325. Coil 323 may be a unitary (i.e., one-piece) hollow member of generally cylindrical shape made from a coiled filament, such as, for example, a stainless steel wire. Coil 323 may be shaped to comprise a proximal portion 327, a distal portion 329, and an intermediate portion 331. Proximal portion 327 may comprise a plurality of turns 333 that may be spaced from one another relatively closely. By contrast, distal portion 329 may comprise a plurality of turns 335 that may be spaced from one another relatively farther apart, the spacing between turns 335 preferably being sufficient to enable turns 335 to mate with and to be bonded to the turns 339 at a distal end of core wire 315 in a fashion analogous to that described above for snare device 11. Intermediate portion 331 may space apart proximal portion 327 and distal portion 329 by a sufficient distance to define a side opening 341, side opening 341 being dimensioned to permit core wire 315 to freely pass therethrough.

Tube 325, which may be, for example, a braided microcatheter, may be coaxially inserted within and bonded to proximal portion 327 of support 321 to provide support to proximal portion 327.

Snare device 311 may further comprise a radiopaque coil 351 coaxially inserted over at least a portion of the looped portion of core wire 315. Radiopaque coil 351 may be used to facilitate visualization of the looped portion of core wire 315.

Snare device 311 may be used in a generally analogous fashion to snare device 11.

Figure 6:
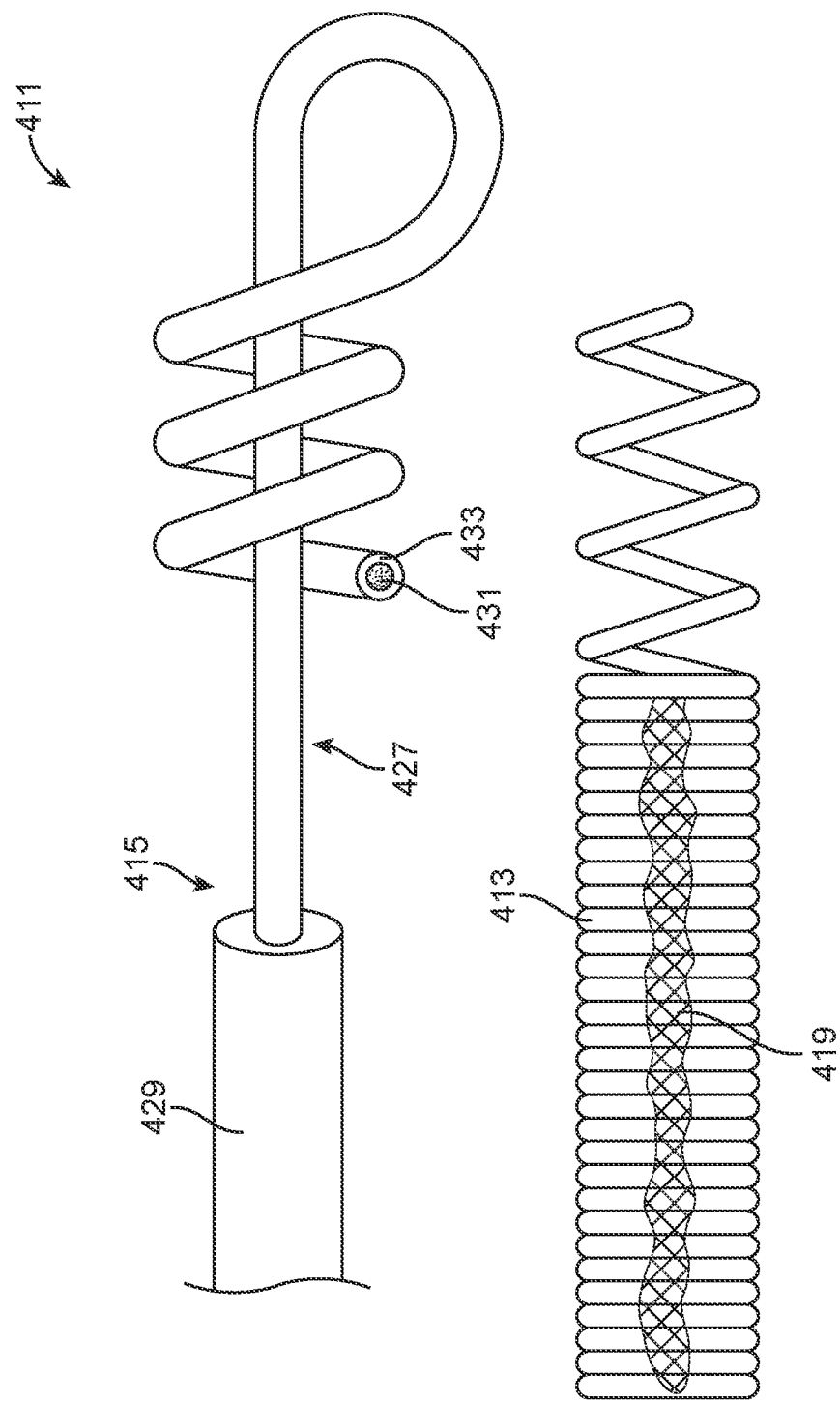
FIG. 6 is a fragmentary, partly exploded, perspective view of a fifth embodiment of a snare device constructed according to the teachings of the present invention.

Referring now to FIG. 6, there is shown a fragmentary, partly exploded, perspective view of a fifth embodiment of a snare device, the snare device being constructed according to the teachings of the present invention and being represented generally by reference numeral 411. Details of snare device 411 that are discussed elsewhere in this application or that are not critical to an understanding of the invention may be omitted from FIG. 6 and/or from the accompanying description herein or may be shown in FIG. 6 and/or described herein in a simplified manner.

Snare device 411, which may be similar in certain respects to snare device 11, may comprise a support 413, a core wire 415, and a handle (not shown). Support 413 may be similar to support 13, except that a thin adhesive layer 419, which may serve a function similar to that of sleeve 131 of snare device 111, may be applied over at least a portion of the exterior of support 413.

Core wire 415, which may be similar in overall size and shape to core wire 15, may comprise a plurality of components. For example, in the present embodiment, core wire 415 may comprise a length of drawn filled tubing 427 and an outer tube 429. Drawn filled tubing 427 may comprise a core 431 and a sheath 433. Core 431 may comprise a radiopaque material (e.g., Pt, Pd, Ag, Au, Ta). Sheath 433, which may coaxially surround core 431, may comprise Nitinol or a similar material. Outer tube 429, which may serve to add stiffness to drawn filled tubing 427 so as to prevent its flexure during pushing, may coaxially surround and be bonded to a proximal portion of drawn filled tubing 427. Outer tube 429 may be made of a material, such as Nitinol, polyimide, PEBAX, NYLON, and a PTFE composite. A PTFE coating (not shown) may be applied to the exterior of outer tube 429 to enhance its lubricity.

Snare device 411 may be used in a generally analogous fashion to snare device 11.

One advantage of snare device 411 is that, by incorporating radiopaque material into the core wire, itself, there is no need to position a radiopaque coil around the exterior of the core wire. This may enable the overall diameter of the distal end of snare device 411 to be very small, for example, as small as 0.014 inch.

Figure 7:
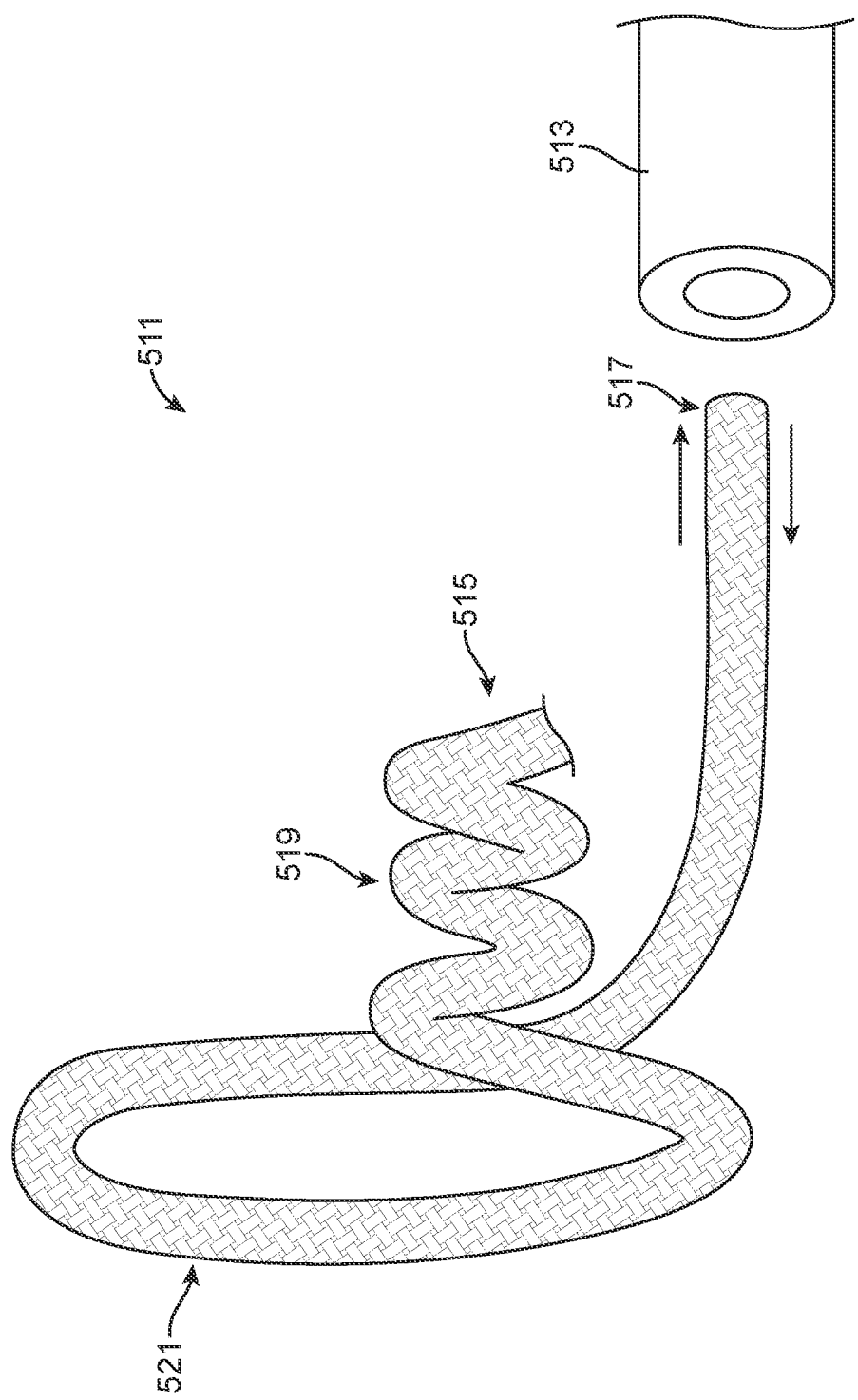
FIG. 7 is a fragmentary exploded perspective view of an alternative embodiment of a core wire.

Referring now to FIG. 7, there is shown an alternative embodiment of a core wire constructed according to the teachings of the present invention, the core wire being represented generally by reference numeral 511. Details of core wire 511 that are discussed elsewhere in this application or that are not critical to an understanding of the invention may be omitted from FIG. 7 and/or from the accompanying description herein or may be shown in FIG. 7 and/or described herein in a simplified manner.

Core wire 511, which may be used in place of any of core wires 15, 121, 215, 315, and 415, may comprise a proximal member 513 and a distal member 515. Proximal member 513 may comprise a tube that may provide some support to distal member 515, thereby enhancing the pushability of core wire 511. Distal member 515 may comprise a wire strand or cable, which may be made of Nitinol or the like. A proximal portion 517 of distal member 515 may be coaxially inserted into and fixedly mounted within proximal member 513. A distal portion of distal member 515 may be formed into a coiled section 519 and a loop 521. Although not shown, a radiopaque coil or the like may be inserted over loop 521.

Some of the advantages of a wire strand or cable like distal member 515, as compared to a single wire of the same diameter, are the following: increased flexibility (less stiffness); more damage resistance; and better fatigue performance under cyclic flexure. (See Reedlunn et al., "Superelastic shape memory alloy cables: Part I—Isothermal tension experiments," *International Journal of Solids and Structures*, 50:3009-3026 (2013), which is incorporated herein by reference).

Referring now to FIGS. 8A through 8C, there is shown a sequence of views that illustrate one embodiment of a method of assembling a snare device according to the teachings of the present invention. Details of the method that are discussed elsewhere in this application or that are not critical to an understanding of the invention may be omitted from one or more of FIGS. 8A through 8C and/or from the accompanying description herein or may be shown in FIGS. 8A through 8C and/or described herein in a simplified manner.

As seen in FIG. 8A, the method may begin by providing a support 613, a core wire 615, and a mandrel 617. Support 613, which may be similar to support 13, may comprise a stainless steel coil with a distal stretch 614. Core wire 615, which may be similar to core wire 15, may comprise a Nitinol wire that is shaped to include a proximal portion 621, a distal portion 623, and an intermediate portion 625. Proximal portion 621 may have a comparatively larger filamentary diameter, distal portion 623 may have a comparatively smaller filamentary diameter, and intermediate portion 625 may have a filamentary diameter that tapers steadily from that of proximal portion 621 to that of distal portion 623. Distal portion 623 may be shaped, for example, through heat-setting, to include a coiled section 629, wherein coiled section 629 may have a size and shape complementary to that of distal stretch 614 of support 613. Mandrel 617 may comprise a generally cylindrical member having a diameter that may be larger than that of proximal portion 621 of core wire 615.

Next, as can be seen in FIG. 8B, mandrel 617 may be inserted coaxially through support 613 and through the coiled section 629 of core wire 615, and distal stretch 614 of support 613 and coiled section 629 of core wire 615 may be mated and bonded together (with an adhesive 630), wherein distal stretch 614 and coiled section 629 may jointly define a hollow joint.

Next, as can be seen in FIG. 8C, mandrel 617 may be removed, and a proximal end 633 of core wire 615 may be inserted into the hollow joint defined by distal stretch 614 and coiled section 629 and, thereafter, through the remainder of support 613.

As noted above, for example, in connection with snare device 311, it may be desirable to position one or more radiopaque coils around the looped portion of the core wire in order to facilitate the visualization of the looped portion of the core wire. Referring now to FIGS. 9A and 9B, there is shown a sequence of views that illustrate one embodiment of a method for mounting one or more radiopaque coils over a core wire according to the teachings of the present invention. Details of the method that are discussed elsewhere in this application or that are not critical to an understanding of the invention may be omitted from one or more of FIGS. 9A and 9B and/or from the accompanying description herein or may be shown in FIGS. 9A and 9B and/or described herein in a simplified manner.

As can be seen in FIG. 9A, the method may begin by providing a core wire 711. Core wire 711, which may be made of Nitinol or the like, may be shaped to include a proximal portion 713 of comparatively larger diameter, a distal portion 715 of comparatively smaller diameter, and an intermediate portion 717 that steadily tapers in diameter from proximal portion 713 to distal portion 715. A first radiopaque coil 721 and a second radiopaque coil 723 may be coaxially inserted over and bonded to distal portion 715 of core wire 711, with first radiopaque coil 721 having its proximal end positioned at the interface of distal portion 715 and intermediate portion 717 and with second radiopaque coil 723 having its proximal end abutting the distal end of first radiopaque coil 721. First radiopaque coil 721 may be closely wound and may have an outer diameter that is substantially equal to the diameter of proximal portion 713. Second radiopaque coil 723 may have an outer diameter that exceeds that of proximal portion 713.

Then, as can be seen in FIG. 9B, the method may continue with a shape setting step in which the distalmost portion of distal portion 715 may be wrapped around a mandrel and heat set to form a coiled structure.

Referring now to FIGS. 10A and 10B, there is shown a sequence of views that illustrate another embodiment of a method for mounting one or more radiopaque coils over a core wire according to the teachings of the present invention. Details of the method that are discussed elsewhere in this application or that are not critical to an understanding of the invention may be omitted from one or more of FIGS. 10A and 10B and/or from the accompanying description herein or may be shown in FIGS. 10A and 10B and/or described herein in a simplified manner.

As can be seen in FIG. 10A, the method may begin by shape setting a core wire 811. More specifically, core wire 811, which may comprise a Nitinol wire of constant filamentary diameter over its length, may be wrapped around a mandrel 812, held in place with a spring clamp 813, and heat set to form a coiled structure.

Then, as can be seen in FIG. 10B, the method may continue with distally sliding a first radiopaque coil 821 and a second radiopaque coil 823 coaxially over the straight portion of core wire 811 and bonding coils 821 and 823 to core wire 811. First radiopaque coil 821, which may be positioned more distally, may have a comparatively greater outer diameter, and second radiopaque coil 823, which may be positioned more proximally, may have a comparatively lesser outer diameter. Next, a tube 825, which may endow core wire 811 with greater pushability, may be inserted over and bonded to a proximal portion of core wire 811.

Figure 11:
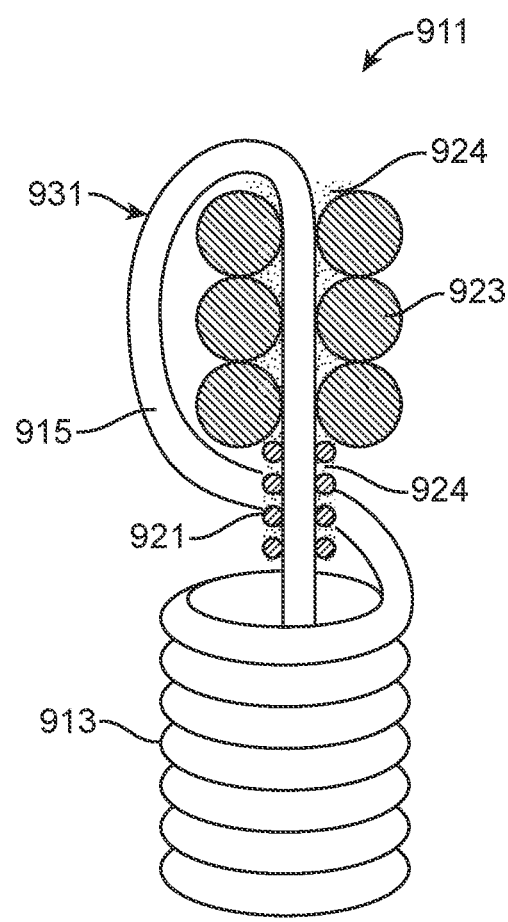
FIG. 11 is a perspective view of a sixth embodiment of a snare device constructed according to the teachings of the present invention.

Referring now to FIG. 11, there is shown a fragmentary perspective view of a sixth embodiment of a snare device, the snare device being constructed according to the teachings of the present invention and being represented generally by reference numeral 911. Details of snare device 911 that are discussed elsewhere in this application or that are not critical to an understanding of the invention may be omitted from FIG. 11 and/or from the accompanying description herein or may be shown in FIG. 11 and/or described herein in a simplified manner.

Snare device 911 may be similar in certain respects to snare device 11. For example, snare device 911 may comprise a support 913, which may be similar or identical to support 13, and may also comprise a core wire 915, which may be similar or identical to core wire 915. (Snare device 911 may additionally comprise a handle (not shown) similar or identical to handle 17.)

Snare device 911 may differ from snare device 11 is that snare device 911 may additionally comprise two radiopaque coils 921 and 923, which may be coaxially inserted over and bonded, with adhesive 924, to core wire 915. Radiopaque coil 921 may be dimensioned so that its outer diameter is less than the inner diameter of support 913, thereby enabling radiopaque coil 921, as well as the portion of core wire 915 surrounded by radiopaque coil 921 to be drawn into the central lumen of support 913. By contrast, radiopaque coil 923 may be dimensioned so that its outer diameter is greater than the inner diameter of support 913. As a result, radiopaque coil 923, as well as the portion of core wire 915 surrounded by radiopaque coil 923, may not be drawn into support 913. Consequently, radiopaque coil 923 may serve to limit the extent to which core wire 915 may be drawn into support 913 and, in so doing, may serve to limit the loop bend radius 931 of core wire 915. This is advantageous because, if the loop bend radius 931 becomes too small, core wire 915 might fracture, especially after several cycles of expanding and contracting the loop.

As noted above, the snare device of the present invention may be used to capture an object in a space. An alternative use for the snare device of the present invention is as anchored guidewire. For example, referring now to FIGS. 12A through 12E, the use of a snare device of the present invention for use as an anchored guidewire within a body lumen, such as a blood vessel, is shown.

Figure 12A:
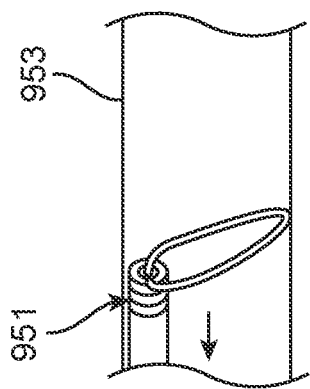
FIGS. 12A through 12E are simplified fragmentary views, partly in section, showing the use of a snare device according to the present invention for use as an anchored guidewire.
Figure 12B:
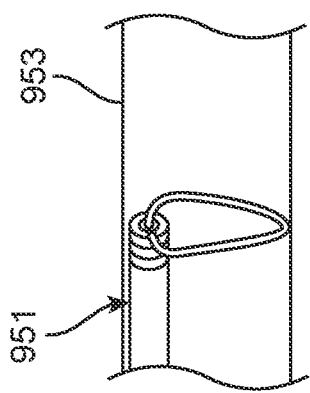
Figure 12C:
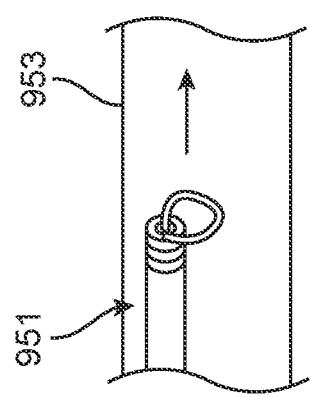
Figure 12D:
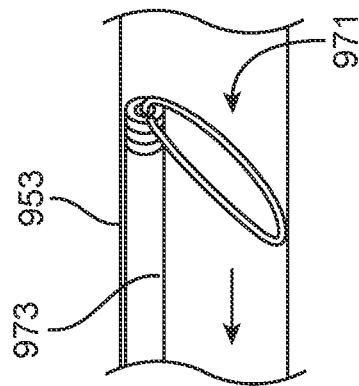
Figure 12E:
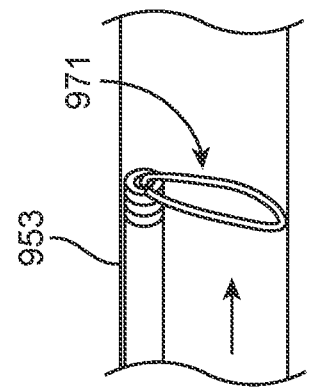

To this end, FIG. 12A shows a snare device 951 being advanced to a desired location within a blood vessel 953. As can be seen, during such advancement, the loop of snare device 951 is preferably in a contracted state. In FIG. 12B, snare device 951 is located at the desired location, and its loop is expanded until it pushes against blood vessel 953. As can be seen, the angle of the loop is generally perpendicular to the longitudinal axis of the blood vessel 953. This may be undesirable as a proximally directed force may cause the loop to become dislodged, as is shown in FIG. 12C. Consequently, it may be desirable to use a snare device like snare device 971, which has a loop that is angled slightly proximally, as is shown in FIG. 12D. In this manner, when a proximally directed force is applied, the loop will more securely anchor within the blood vessel. As can be appreciated, such anchoring may be improved by wrapping a coil coaxially around the loop. With snare device 971 thus anchored, support 973 may be used as a guidewire to deliver a medical instrument or the like to the space just proximal to the loop.

Another potential application for the snare device of the present invention may be in using the loop to cauterize.

Referring now to FIG. 13, there are shown various exemplary design options and dimensions for the snare device of the present invention.

It is to be understood that features of the various snare devices disclosed herein may be combined in various ways.

Additional objects, features, and advantages of the present invention are set forth below.

A flexible longitudinal Support defining an axis and a lumen
    The support having a constrained length (not expanding or shrinking)
    The support including a helical gap at the distal end
    The support including an open lumen at the distal end or near the distal end as proximal end
        The Support composed of a metallic coil and a sleeve (mast and stay)
            The sleeve secured to the coil either on the outside or within the coil The sleeve supporting the coil integrity
The sleeve ensuring the defined length of the support
The sleeve allowing a desired flexibility in the coil
The sleeve composed of a polymer
  The outer sleeve polymer made with Nylon, Pebax, PET or PTFE
  The inner sleeve polymer being a PI tube, Pebax tube or composite that includes PTFE on the inner diameter
  The sleeve being formed by adding an adhesive to bridge the coils
The Support comprising a tube
The tube being made of metal (e.g., SS, CoCr, Nitinol)
  The tube being slotted as required to provide flexibility
The tube being made of a composite polymer
  The composite including metal (braid or coil)
  The composite including a distal member for receiving a helical wire
A flexible Core Wire having a distal end and a proximal end, the core wire largely constrained within and extending through the Support at the distal end and the proximal end
  The core wire distal end being formed into a helical shape that loops back, mates and joins to the Support distal end, having essentially the same helical pitch, and fits within the OD/ID constraints of the Support distal end.
  The core wire made of a super-elastic metallic wire
    The core wire made of nitinol
    The core wire composed of a nitinol tube including a RO material
    The core wire distal region proximal to the helical shape being formed into a loop shape that is oriented at an angle away from the Support axis
  The core wire distal region having a smaller profile than the proximal region
  The core wire made of a stiff polymeric or composite material such as polyimide/PTFE and/or polyimide/metal braid/PTFE and/or nylon/wire
  The core wire having a constant diameter and covered with a tube more proximally, the tube serving to stiffen the Core member for advanceability
A small coil made of a radiopaque (RO) material surrounding and joined to the distal core wire loop region having an outer diameter that fits and slides within the support inner diameter. To slide more easily within the support coil, it would be advantageous to manufacture the RO coil having a wind angle that is opposite the support coil (e.g., Support coil being Right hand wound, RO coil being Left hand wound)
A second RO coil surrounding and joined to the distal core wire loop having an outer diameter that is larger than the inner diameter of the support, which limits the size of the loop so that the loop size does not become too small and retract fully within the support.
The proximal end of the Core being advanceable and retractable by a clinician to form variable loop sizes at the distal end suitable for capturing desired objects
  The core wire proximal end extending beyond the support having a tubular covering joined to the core and positioned so as to provide a stop against the Support that limits the size of the loop by limiting the amount that the core may be advanced The embodiments of the present invention described above are intended to be merely exemplary and those skilled in the art shall be able to make numerous variations and modifications to it without departing from the spirit of the present invention. For example, features from one or more of the embodiments described above may be combined in various permutations. All such variations and modifications are intended to be within the scope of the present invention as defined in the appended claims.

What is claimed is:

1. A snare device, the snare device comprising:
(a) a support, the support comprising a proximal portion terminating in a proximal end, a distal portion terminating in a distal end, and a lumen, the lumen extending distally from the proximal end;
(b) a core wire, the core wire being flexible and comprising a proximal portion and a distal portion, wherein the distal portion of the core wire and the distal portion of the support are complementarily shaped and dimensioned helical structures and are fixedly fitted together, wherein the core wire forms a loop extending away from the distal end of the support, and wherein the core wire passes through the lumen and emerges from the proximal end of the support, and wherein the loop is adjustable in size by moving the proximal end of the core wire relative to the proximal end of the support; and
(c) further comprising two radiopaque coils coaxially mounted over the core wire, a first of the two radiopaque coils being positioned more proximally on the core wire and having an outer diameter smaller than the diameter of the lumen, a second of the two radiopaque coils being positioned more distally on the core wire and having an outer diameter greater than the diameter of the lumen.

2. The snare device as claimed in claim 1, wherein the lumen of the support has a longitudinal axis and wherein the loop extends generally along the longitudinal axis.

3. The snare device as claimed in claim 1, wherein the lumen of the support has a longitudinal axis and wherein the loop extends generally perpendicular relative to the longitudinal axis.

4. The snare device as claimed in claim 1, wherein the lumen of the support extends from the proximal end of the support to the distal end of the support and wherein the core wire passes through the distal end of the support.

5. The snare device as claimed in claim 1, wherein the support has a side opening and wherein the core wire passes through the side opening.

6. The snare device as claimed in claim 1, wherein the support comprises a coil, the coil comprising a proximal portion having closely spaced turns and a distal portion having spaced apart turns.

7. The snare device as claimed in claim 1, wherein the support comprises a coil and a hypotube, the coil being mounted on a distal portion of the hypotube.

8. The snare device as claimed in claim 1, further comprising a handle and wherein the proximal portion of the core wire is coupled to the handle.

9. The snare device as claimed in claim 1, further comprising a sleeve, wherein the sleeve is positioned coaxially around the support.

10. The snare device as claimed in claim 1, further comprising a tube, wherein the tube is positioned coaxially within the support.

11. The snare device as claimed in claim 1, wherein the core wire consists of a single filament.

12. The snare device as claimed in claim 1, wherein the core wire comprises a drawn filled tube coaxially surrounding a radiopaque wire.

13. The snare device as claimed in claim 12, wherein the core wire further comprises a tube coaxially surrounding a proximal portion of the drawn filled tube.

14. The snare device as claimed in claim 1, wherein the core wire comprises a wire cable and a tube, the tube being coaxially surrounding a proximal portion of the wire cable.

15. The snare device as claimed in claim 1, wherein the distal portion of the core wire and the distal portion of the support are flush with one another.

16. The snare device as claimed in claim 1, wherein the two radiopaque coils have equal inner diameters and wherein each of the two radiopaque coils is bonded to the core wire.

* * * * *